United States Patent
Augustijn et al.

(10) Patent No.: US 7,651,480 B2
(45) Date of Patent: Jan. 26, 2010

(54) ASSEMBLY OF A NEEDLE AND A FLUID SUPPLY DEVICE AND METHODS OF THEIR USE

(75) Inventors: Cathelijne Dine Augustijn, Heemsted (NL); Christiaan Johannes Snijders, Wassenaar (NL); Wilhelmus Sigebertus C. J. M. Van der Pol, Delft (NL)

(73) Assignee: Erasmus Universiteit Rotterdam, Rotterdam (NL)

(*) Notice: Subject to any disclaimer, the term of this patent is extended or adjusted under 35 U.S.C. 154(b) by 1598 days.

(21) Appl. No.: 10/472,137

(22) PCT Filed: Sep. 17, 2001

(86) PCT No.: PCT/NL01/00690

§ 371 (c)(1),
(2), (4) Date: Sep. 12, 2003

(87) PCT Pub. No.: WO02/22201

PCT Pub. Date: Mar. 21, 2002

(65) Prior Publication Data
US 2004/0147879 A1    Jul. 29, 2004

(30) Foreign Application Priority Data
Sep. 15, 2000 (NL) .................................. 1016207

(51) Int. Cl.
*A61M 5/00* (2006.01)
*A61M 39/00* (2006.01)
*A61M 39/10* (2006.01)
*A61M 25/16* (2006.01)
*A61M 25/18* (2006.01)

(52) U.S. Cl. .................. 604/240; 604/239; 604/533

(58) Field of Classification Search .......... 604/239–241, 604/506, 507, 533, 539, 905
See application file for complete search history.

(56) References Cited

U.S. PATENT DOCUMENTS

| 5,286,067 A | 2/1994 | Choksi |
| 5,514,114 A * | 5/1996 | Soto-Tolosa et al. ........ 604/275 |
| 5,830,188 A * | 11/1998 | Abouleish .................... 604/158 |
| 6,200,291 B1 * | 3/2001 | Di Pietro ..................... 604/117 |

FOREIGN PATENT DOCUMENTS

| EP | 0 701 837 A1 | 3/1996 |
| GB | 2 072 288 | 9/1981 |
| WO | WO 98/10808 | 3/1998 |

* cited by examiner

*Primary Examiner*—Nicholas D Lucchesi
*Assistant Examiner*—Rebecca E Eisenberg
(74) *Attorney, Agent, or Firm*—Hoffman & Baron, LLP

(57) ABSTRACT

Assembly of a needle (1) and a fluid supply device (7b), the needle (1) being provided with needle coupling means (2), the supply device (7b) being provided with a nozzle (9b), the needle coupling means (2) comprising a standardized construction with standardized internal dimensions according to the Luer standard, the needle coupling means (2) further comprising a projection (5), which renders fitting the needle (1) to a supply device with a nozzle (7a) arranged for cooperation with needle coupling means having standardized construction and dimensions according to the Luer standard impossible, the nozzle (7b) of the supply device (9b) being lengthened relative to a standardized nozzle (9a), such that the needle coupling means (2) with projection (5) can still be coupled to the lengthened nozzle (9b). The invention further relates to a needle (1), a syringe (7b), a method for performing an intraneural puncture and a method for preparing an insertion device for intraneural administration.

18 Claims, 4 Drawing Sheets

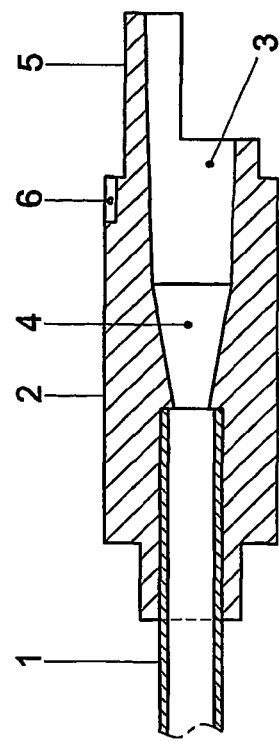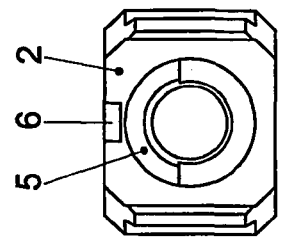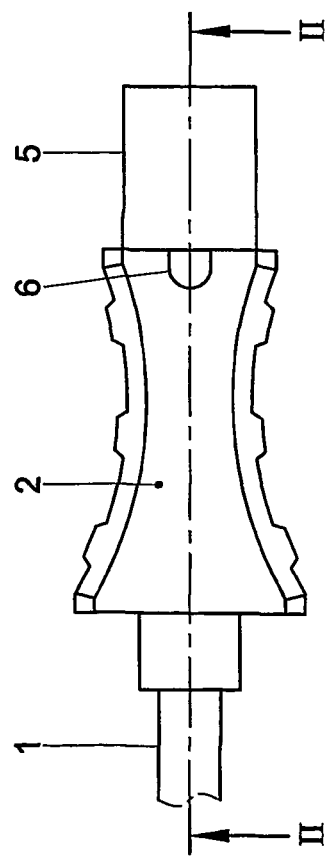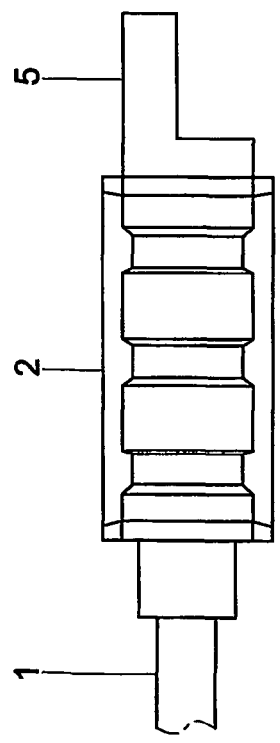

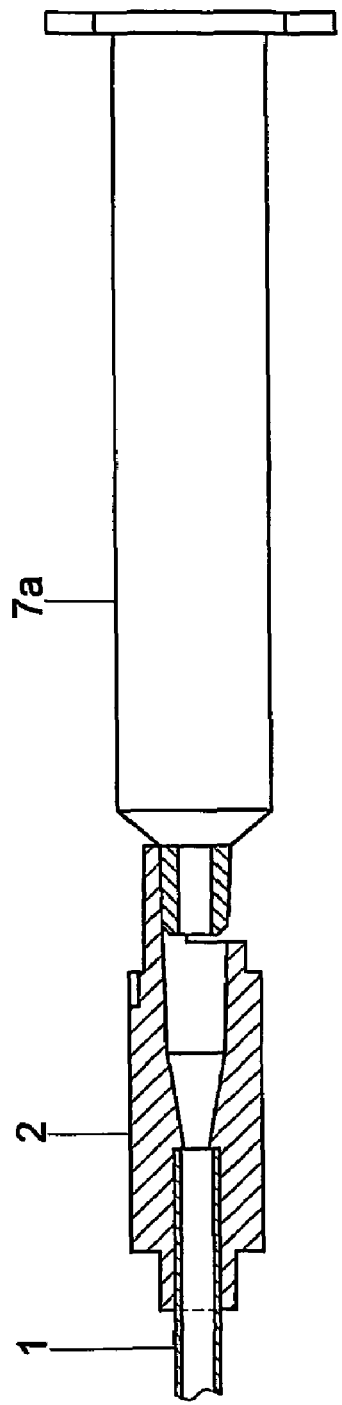
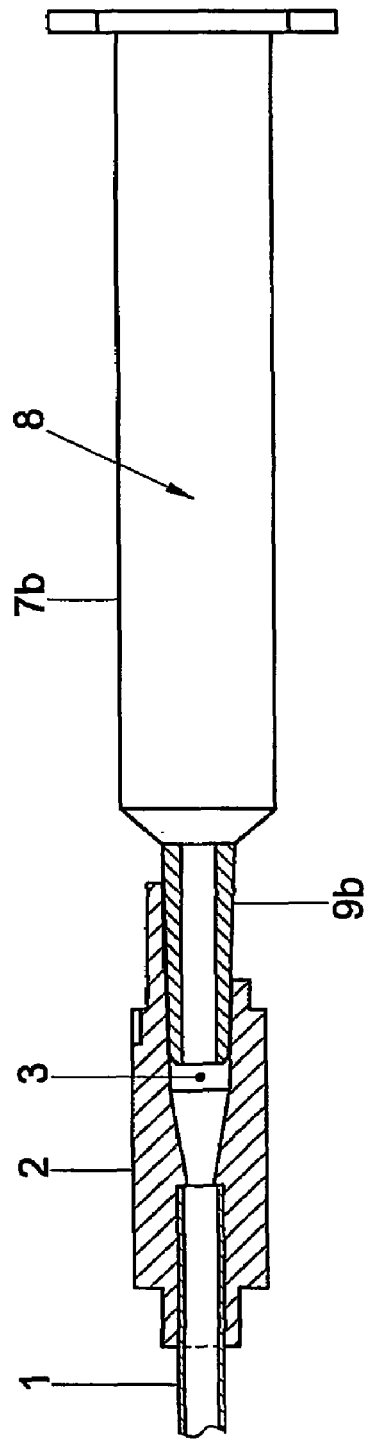

ASSEMBLY OF A NEEDLE AND A FLUID SUPPLY DEVICE AND METHODS OF THEIR USE

This application is the U.S. National Phase of International Application Number PCT/NL01/00690 filed on 17 Sep. 2001, which is incorporated herein by reference.

BACKGROUND OF THE INVENTION

The invention relates to an assembly of a needle and a fluid supply device, the needle being provided with needle coupling means, the supply device being provided with a nozzle, the needle coupling means comprising a standardized construction with standardized dimensions according to the Luer standard.

Such an assembly is known from practice and is used for administering a medicine to a patient. This involves the medicine being introduced, with the aid of the fluid supply device, via the needle, into an administering location of the patient. The supply device can, for instance, comprise a syringe which can be coupled directly with the nozzle to the needle coupling means of the needle. Such a syringe can also be indirectly brought into fluid communication with the needle coupling means, with the aid of, for instance, a fluid tube or hose which is also provided with a nozzle. In this last manner, also a fluid reservoir such as a drip can be brought in fluid communication with the needle. The known assembly can be used in combination with other means which can be used optionally, such as for instance suction needles, filters, regulating means such as taps, and connecting means arranged to bring various fluid reservoirs into fluid communication with one needle. To that end, these means are also provided with the standardized construction with standardized dimensions according to the Luer standard, so that they can cooperate mutually exchangeably with the needle coupling means. According to the above-mentioned Luer standard, the coupling means comprise conical fittings which are provided with a 6% cone as described in the NEN-ISO 594-1 standard.

The use of the known assembly comprises different operations. First, the supply device is filled with fluid containing, for instance, a medicine. The filling is generally done by a pharmacist or a pharmacist's assistant in a pharmacy. Subsequently, the medicine can be administered, which is performed, for instance, in a sterile surgery or operating theatre of a hospital. Administration is generally performed by specially trained staff, such as doctors or nurses. For the purpose of administering the medicine, the needle is inserted into a predetermined administering location of the patient. Then, the supply device is brought into fluid communication with this needle via the needle coupling means. Finally, fluid with the medicine can be introduced into the patient at the desired location by operating the supply device. An administering location can for instance be an intramuscular, intravenous or intraneural, i.e. at least an intrathecal or intradural, location which corresponds to administration into a muscle, a vein or the nervous system, respectively. Intraneural administration can, for instance, be carried out intrathecally using, generally, a lumbar puncture needle.

A drawback of this known assembly is that it can be used for any administering location. Hence, the situation may arise that a medicine destined to be introduced in a first administering location of a patient is erroneously introduced into another administering location. Such an error can have grave, even fatal consequences. One of the most notorious administering errors comprises the intraneural administration of the medicine vincristine to be administered intravenously. A child suffering from leukemia can be subjected to a chemotherapeutic treatment, for which, according to a certain treatment protocol, the medicine vincristine has to be administered on the same day as a second medicine, to be administered intraneurally. Then, it happens that the two different medicines are confused, so that vincristine is administered intraneurally, and the child may die. The confusion of intraneurally and intravenously to be administered medicines may already have happened during the filling of the fluid supply device, or may happen in the surgery during administration.

A proposal for a solution to this problem of confusion is known from an article of R. A. Anderson et al., published in the journal "Medical and Pediatric Oncology" 1999, pages 401 and 402, issue 32. There, the coupling means of a syringe is provided with a detachable marking element to indicate that the syringe contains a medicine which may, during administration, only be administered intraneurally. A drawback of this proposal is that different pharmacists, doctors and/or nurses of different pharmacies or hospitals, respectively, may, in practice, have come to different agreements regarding the meaning of such a marking. A different person may, for instance, use the marking to indicate that the syringe contains a medicine destined for non-intraneural administration.

According to the same article, a second solution is to provide both the needle coupling means of the needle and the nozzle of the syringe with a non-standardized, particular shape or size, such that cooperation with, respectively, a nozzle or needle coupling means having a standardized construction and dimensions according to the Luer standard, is impossible. As a result, during administration, the confusion of two medicines is no longer possible, at least when the different syringes have been correctly filled with the different medicines. This solution has the drawback that means to be used optionally which have a standardized construction and dimensions according to the Luer standard, such as suction needles, filters and the like, cannot cooperate with these adapted needle coupling means and nozzles. For that reason, before use, such standardized treatment means have to be replaced with new treatment means with adapted coupling constructions, which entails relatively high replacement costs.

The present invention contemplates solving the above-mentioned drawbacks of the assembly while maintaining its advantages. Hence, the invention provides an assembly with which the risk that, in use, a medicine destined for non-intraneural administration is mistakenly administered intrathecally via the needle, is very small. Further, the needle and administration device according to the invention can be used in combination with a number of other treatment means, standardized according to the Luer standard.

SUMMARY OF THE INVENTION

To this end, the assembly according to the invention is characterized in that the needle coupling means also comprise a projection which renders it impossible for the needle to be fitted to a supply device with a nozzle arranged for cooperation with needle coupling means with a standardized construction and dimensions according to the Luer standard, while the nozzle of the supply device is lengthened relative to a standardized nozzle, such that the needle coupling means with the projection can still be coupled to the lengthened nozzle.

In this manner, a number of treatment means can still cooperate with the needle coupling means and lengthened nozzle, while cooperation of a nozzle arranged to cooperate with needle coupling means having standardized construction and dimensions according to the Luer standard with the needle coupling means is prevented. The assembly is destined to be used for administering only one or a number of medicines in one particular administering location, and is particularly suitable for intraneural administration since the erroneous intraneural administration of a medicine which has to be administered non-intraneurally can be readily prevented.

The invention further relates to a needle provided with needle coupling means, the needle coupling means comprising a standardized construction with standardized dimensions according to the Luer standard, characterized in that the needle coupling means also comprise a projection, which renders it impossible for the needle to be fitted to a supply device with a nozzle arranged for cooperation with needle coupling means with a standardized construction and dimensions according to the Luer standard.

By using this needle for administration in one particular administering location, it can be prevented that, via the needle, a medicine, destined to be administered in another administering location, is erroneously administered by means of the supply device with a nozzle arranged for cooperation with needle coupling means with standardized construction and dimensions.

Additionally, the invention provides a syringe provided with a nozzle, characterized in that the nozzle of the syringe is lengthened relative to the standardized nozzle according to the Luer standard, such that the lengthened nozzle can be coupled to needle coupling means of a needle according to the invention.

This syringe can still cooperate with the needle which is provided with needle coupling means comprising the projection mentioned, such that with this syringe, a medicine can be administered to a patient via that needle. Therefore, the syringe is preferably destined to be filled with a medicine to be administered intraneurally. Moreover, the nozzle of the syringe can cooperate with standardized means such as suction needles provided with a coupling construction according to the Luer standard.

What can be elegantly achieved by providing the needle coupling means with a projection is that it is crystal clear to a user that the needle coupling means cannot cooperate with a standardized Luer nozzle, while in case of cooperation of the needle coupling means with an adapted, lengthened nozzle, use can still be made of the standardized technology of the Luer coupling, in particular the 6% cone. In this manner, well-proven technology can be used for all components of the assembly, so that the assembly according to the invention can be implemented in a relatively low-cost manner and can rapidly and readily be accepted by users. When, in the pharmacy, the syringe with the correct medicine has been prepared, administration of the medicine at an incorrect administering location can presently be avoided.

The invention also relates to a method for performing all intraneural puncture for discharging neural fluid such as cerebrospinal fluid to a collecting reservoir, characterized in that a needle, provided with needle coupling means comprising a channel-shaped projection, is inserted and kept such that the cerebrospinal fluid can flow from the needle and needle coupling means through the channel-shaped projection and is subsequently collected in the collecting reservoir.

Further, the invention provides a method for preparing an insertion device for intraneural administration wherein a needle with a coupling means is coupled to a syringe, characterized in that the syringe with a relatively long nozzle is coupled to the coupling means, in fluid-tight cooperation, the nozzle passing a projection of the coupling means, this projection keeping the nozzle of a standard syringe at a distance from the coupling means, such that, when a standard syringe is used with the coupling means, no fluid-tight connection between the needle and the syringe can be obtained.

What can be prevented by preparing the insertion device according to this method, is that a medicine which is not to be administered intraneurally, is present in a standard syringe, and is still administered intraneurally, which could have fatal consequences.

Further advantageous elaborations of the invention are described in the subclaims.

BRIEF DESCRIPTION OF THE DRAWINGS

The invention will be further elucidated on the basis of an exemplary embodiment and the accompanying drawing.

FIG. 1 shows a top plan view of an exemplary embodiment of a needle;

FIG. 2 shows a cross sectional view along the line II-II of the top plan view represented in FIG. 1;

FIG. 3 shows a front view of the top plan view represented in FIG. 1;

FIG. 4 shows a side view of the front view represented in FIG. 3;

FIG. 13 shows a partly opened front view of the syringe provided with a non-lengthened nozzle in a position moved towards the needle; and FIG. 14 shows a similar front view to FIG. 13 of the syringe provided with a lengthened nozzle in a condition of cooperation with the needle.

DETAILED DESCRIPTION OF THE INVENTION

Figure 5:
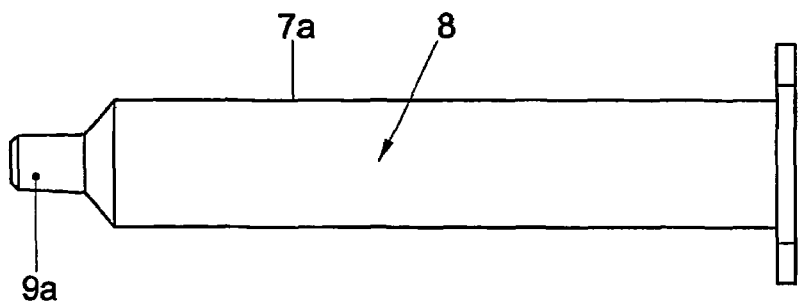
FIG. 5 shows a front view of an exemplary embodiment of a syringe provided with a non-lengthened nozzle.

The exemplary embodiment comprises an assembly destined for administering a medicine present in a fluid to a patient. The assembly is provided with a hollow needle 1 and a syringe 7. The needle 1 is provided in a connector 2, arranged as a needle coupling means according to the Luer standard. Via a fluid channel 4, a conically tapering coupling opening 3 of this connector 2 is in fluid communication with the needle 1. To save space in axial direction, the cone-shaped receiving opening 3 is included in the interior of the connector. On a side of the connector 2 remote from the needle 1 a spacing projection 5 is present. Further, in the same side of the connector 2, there is a positioning recess 6, destined to receive, in use, a positioning projection 13 of a stylet 11 for the purpose of positioning the stylet 11 in the needle 1.

Figure 6:
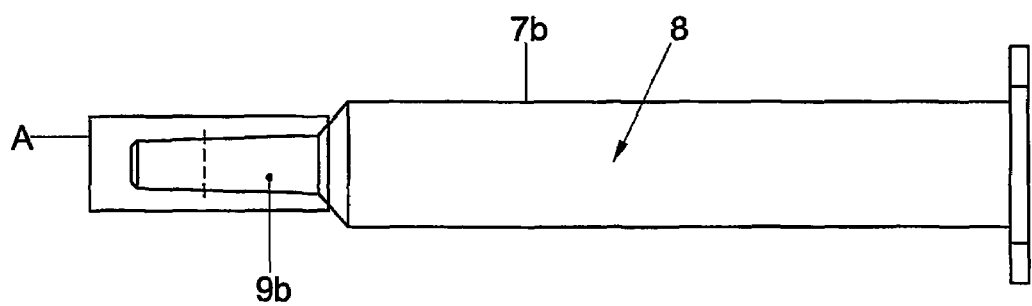
FIG. 6 shows a front view of an exemplary embodiment of a syringe provided with a lengthened nozzle.
Figure 7:
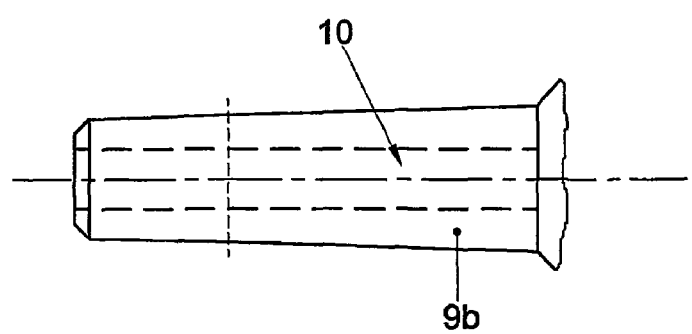
FIG. 7 shows detail A of the front view represented in FIG. 6.
Figure 8:
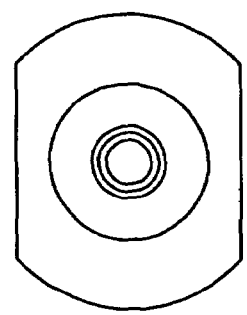
FIG. 8 shows a side view of the front view represented in FIG. 6.
Figure 10:
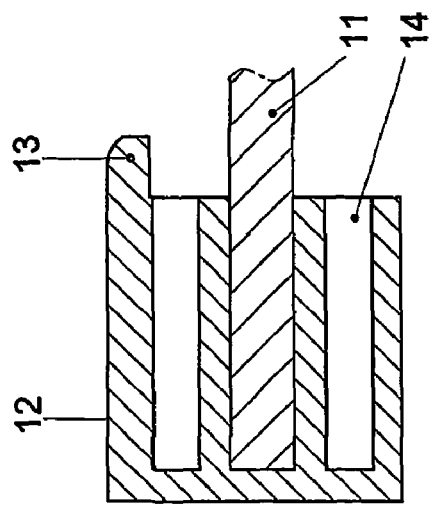
FIG. 10 shows a cross sectional view along the line X-X of the top plan view represented in FIG. 9.
Figure 12:
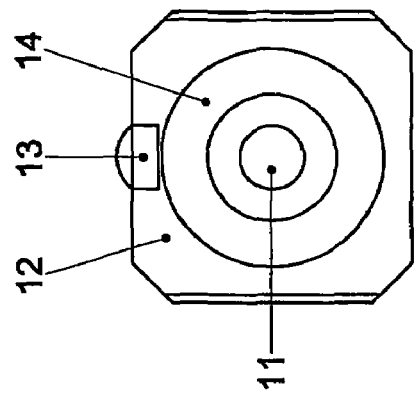
FIG. 12 shows a side view of the front view represented in FIG. 11.
Figure 9:
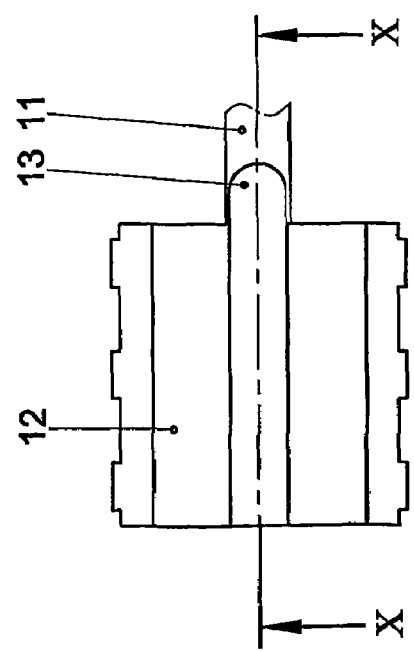
FIG. 9 shows a top plan view of an exemplary embodiment of a part of a stylet with a stop.
Figure 11:
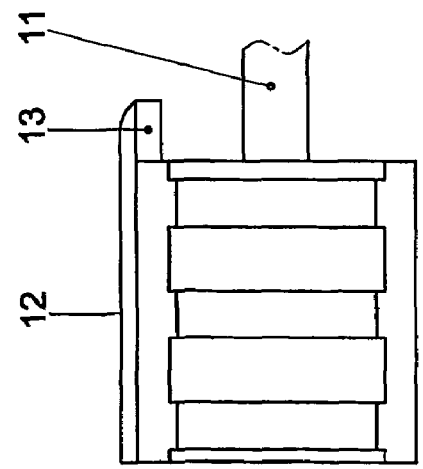
FIG. 11 shows a front view of the top plan view represented in FIG. 9.

FIGS. 5 and 6 show a syringe 7a, 7b, respectively, provided with a non-lengthened and a lengthened nozzle 9a, 9b, respectively, conically tapering according to the Luer standard. Each syringe 7a, 7b comprises a fluid reservoir 8. A fluid passage 10 extends from the fluid reservoir 8, via the nozzle 9a, 9b, to an environment. The difference in length between the nozzles 9a, 9b is indicated with the arrow L.

The needle 1 and the syringe 7b represented in the figures are destined for administration of a medicine in only one administering location, and preferably only for intraneural administration. As indicated in FIG. 13, the spacing projection 5 prevents the syringe 7a provided with a non-lengthened nozzle 9b from being brought in fluid-tight cooperation with the connector 2 of the needle 1. Only the syringe 7b with the lengthened nozzle 9b fits onto the connector 2, while the conical nozzle 9b is close-fittingly slid into the conical coupling opening 3 of the connector 2. As the first mentioned syringe 7a does not fit onto the connector 2 represented, erroneous administration, via the needle 1, of a medicine destined for a different administering location and with which the syringe 7a is filled, is prevented. An additional advantage of the assembly is that it can also be used in combination with a number of other treatment means. For instance, the lengthened nozzle 9b of the syringe 7b can be used with a suction needle (not shown) provided with a coupling construction according to the Luer standard.

Further, the needle 1 can be used to perform an intraneural puncture for discharging a neural fluid such as cerebrospinal fluid to a collecting reservoir. Here, the needle 1 can be inserted and held such, that the cerebrospinal fluid can flow via the needle 1 and the connector 2 to the spacing projection 5. As the projection 5 is channel-shaped, the fluid can flow through the projection 5 and be discharged to the collecting reservoir which is held under the downstream end of the projection 5.

During the insertion of the needle and/or during the performance of such a puncture, generally, a stylet 11 is arranged in the needle 1, which is represented in FIGS. 9-12. The stylet 11 prevents contaminations from ending up in the needle 1 during the insertion of the needle 1 into the patient. To this end, the stylet 11 is designed such that it can be passed through the needle 1 to close off the inside space of the needle. An end of the stylet 11 is provided with a stop 12. This stop 12 comprises a cylindrical recess 14, and is provided on a side proximal to the stylet with the positioning projection 13 mentioned. The stylet 11 can be positioned in the needle 1 with the aid of the positioning projection 13 and recess 6. After insertion of the needle 1 the stylet 11 can be removed from the needle 1 again.

It is self-evident that the invention is not limited to the exemplary embodiment described, but that various modifications are possible within the framework of the invention.

What is claimed is:

1. An assembly of a needle and a fluid supply device, the needle including a needle coupling, the supply device including a lengthened nozzle, wherein the needle coupling includes a 6% conical taper in accordance with a standardized construction and standardized internal dimensions wherein the needle coupling includes a projection, which renders it impossible to fit the needle to another supply device with a non-lengthened nozzle arranged for cooperation with the needle coupling, the lengthened nozzle being longer than the non-lengthened nozzle, wherein the needle coupling can still be coupled to the lengthened nozzle, wherein the lengthened nozzle extends more than 10 mm from a free end of a fluid reservoir of the supply device.

2. An assembly according to claim 1, wherein the length of the nozzle is at least 13 mm, the length of the projection from the needle coupling to a free end of the projection being at least approximately 6 mm.

3. An assembly according to claim 1, wherein the projection extends along a circumference of a coupling opening of the needle coupling which is arranged for cooperation with the lengthened nozzle, the projection extending at most along half of the circumference.

4. An assembly according to claim 1, wherein the projection is channel-shaped such that in use, fluid coming from the needle and the needle coupling can be discharged via the channel-shaped projection to an environment for the purpose of collecting the fluid.

5. A needle provided with a needle coupling, wherein the needle coupling includes an aperture for receiving a lengthened fluid supply nozzle, the needle coupling including a projection extending from the aperture and away from the needle, wherein the projection prevents the needle from being fitted on a supply device with a nozzle, wherein a length of the nozzle is less than that of the projection.

6. A needle according to claim 5, wherein the length of the projection, from the needle coupling to a free end of the projection is at least approximately 6 mm.

7. A needle according to claim 5, wherein the projection extends along a circumference of a coupling opening of the needle coupling which is arranged for cooperation with the nozzle, the projection extending at most along half of the circumference.

8. A needle according to claim 5, wherein the projection is of a channel-shaped design such that, in use, fluid coming from the needle and the needle coupling can be discharged via the channel-shaped projection to an environment.

9. A syringe provided with a syringe nozzle, wherein the syringe nozzle extends more than 10 mm from a free end of a fluid reservoir of the syringe, whereby the syringe can be coupled to the needle coupling of a needle according to claim 5.

10. A syringe according to claim 9, wherein the length of the nozzle from the free end to the reservoir is at least 13 mm.

11. A method for performing an intraneural puncture for discharging a neural fluid to a collecting reservoir, the method comprising:
providing a needle including a needle coupling, the needle coupling including a channel-shaped projection extending from a needle coupling aperture,
inserting a collecting reservoir nozzle past the channel-shaped projection into the coupling aperture, whereby neural fluid can flow from the needle and the needle coupling through the channel-shaped projection and
inserting the needle in a patient for collecting neural fluid in the collecting reservoir.

12. The method according to claim 11, wherein the collecting reservoir nozzle extends more than 10 mm from an end of the collecting reservoir.

13. The method according to claim 11, wherein the coupling aperture is disposed at a first axial end of the needle coupling, the needle being coupled to the needle coupling at an opposed second axial end of the needle coupling.

14. The method according to claim 13, wherein the channel-shaped projection extends at least approximately 6 mm from the coupling aperture.

15. A method for preparing an insertion device for intraneural administration, the method comprising:
coupling a needle to a non-standard syringe, wherein the needle includes a needle coupling, the non-standard syringe including a nozzle in fluid-tight cooperation with the needle coupling, the nozzle extending past a projection of the needle coupling, which projection keeps the nozzle of a standard syringe at a distance from the needle coupling, such that when using a standard syringe with the needle coupling no fluid-tight connection between the needle and the syringe can be obtained.

16. The method according to claim 15, wherein the needle coupling includes an aperture for receiving the nozzle, the projection extending from the aperture away from the needle coupling toward the non-standard syringe.

17. The method according to claim 16, wherein the projection extends at least approximately 6 mm from the aperture.

18. The method according to claim 15, wherein the nozzle extends more than 10 mm from base of a collection reservoir of the non-standard syringe.

* * * * *